United States Patent [19]

Marraccini et al.

[11] Patent Number: 5,292,961

[45] Date of Patent: Mar. 8, 1994

[54] PROCESS FOR THE PREPARATION OF HALOGENATED POLYETHERS

[75] Inventors: Antonio Marraccini; Giovanni Gustalla, both of Novara; Alessandro Malacrida, Milan; Giorgio Guglielmo, Venice, all of Italy

[73] Assignee: Ausimont S.p.A., Italy

[21] Appl. No.: 71,876

[22] Filed: Jun. 4, 1993

Related U.S. Application Data

[63] Continuation of Ser. No. 860,598, Mar. 30, 1992, abandoned, which is a continuation of Ser. No. 693,020, Apr. 30, 1991, abandoned, which is a continuation of Ser. No. 546,701, Jul. 3, 1990, abandoned, which is a continuation of Ser. No. 361,776, May 26, 1989, abandoned, which is a continuation of Ser. No. 119,169, Nov. 10, 1987, abandoned.

[30] Foreign Application Priority Data

Nov. 14, 1986 [IT] Italy ............................... 22347 A/86

[51] Int. Cl.$^5$ ............................................. C07C 41/06
[52] U.S. Cl. .................................. 568/604; 568/677; 568/676; 568/669; 549/378
[58] Field of Search ............... 568/604, 676, 677, 669

[56] References Cited

U.S. PATENT DOCUMENTS 4,577,044  3/1986  Campbell et al. .

FOREIGN PATENT DOCUMENTS 201871  11/1986  European Pat. Off. .
267626  5/1988  European Pat. Off. .
267627  5/1988  European Pat. Off. .
863504  11/1986  South Africa .

OTHER PUBLICATIONS

South African Patent Journal, Dec. 1986 vol. 19, No. 12 p. 174 & Computer Readout from WPIL.
Kamil et al. Inorg, Chem., 1986 25, 376–380.

*Primary Examiner*—Howard T. Mars
*Attorney, Agent, or Firm*—Morgan & Finnegan

[57] ABSTRACT

Process for the preparation of halogenated polyethers of the general formula:

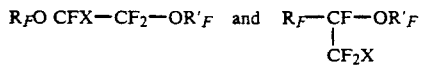

wherein $X = Cl$ or $F$, $R_F$ and $R'_F$ either equal to or different from each other, are selected from fluorinated alkyl radicals with from 1 to 20 carbon atoms, cycloalkyl, heterocyclic, alkylcycloalkyl or cycloalkylalkyl radicals, having from 5 to 20 carbon atoms, said radicals possibly containing also other halogen atoms different from fluorine and possibly ethereal oxygen atoms, by reaction with a fluoroxy or chloroxy compound of the formula: $R'_FOX$ with a fluorovinylether of the general formula: $R_FO-CF=CF_2$.

4 Claims, No Drawings

PROCESS FOR THE PREPARATION OF HALOGENATED POLYETHERS

This is a continuation of co-pending application Ser. No. 07/860,598, filed on Mar. 30, 1992 now abandoned; which is a continuation of application Ser. No. 07/693,020, filed on Apr. 30, 1991, now abandoned; which is a continuation of application Ser. No. 07/546,701, filed on Jul. 3, 1990, now abandoned; which is a continuation of application Ser. No. 07/361,776, filed May 26, 1989, now abandoned; which is a continuation of application Ser. No. 07/119,169, filed Nov. 10, 1987, now abandoned.

The present invention concerns a process for the preparation of a halogenated polyether.

More particularly the polyethers that may be prepared by the process of the present invention are of the general formula:

$$R_FOCFX-CF_2-OR'_F \quad (I)$$

and $$R_FO-CF-OR'_F \quad (II)$$
$$\quad\quad\quad |$$
$$\quad\quad\quad CF_2X$$

wherein X=Cl or F, $R_F$ and $R'_F$, either equal to or different from each other, are selected from fluorinated alkyl radicals having from 1 to 20 carbon atoms; cycloalkyl, heterocyclic, alkylcycloalkyl or cycloalkylalkyl radicals having also other halogen atoms different from fluorine, and possibly etheric oxygen atoms.

From the literature there are known processes for the preparation of the above mentioned polyethers by means of fluorination of the hydrogenated polymers and by the subsequent breaking up of the polymeric chain.

For instance, U.S. Pat. No. 4,523,039 describes a process for the synthesis of the fluorinated polyethers, by direct fluorination with gaseous F$_2$ (of the corresponding hydrogenated polyethers) and by the successive fragmentation of the polymeric chain thus formed in order to produce perfluoropolyethers of a low molecular weight.

Said process has the drawback of requiring very long times, that is, in the order of days, in order for the fluorination to be completed.

Another known process for obtaining the indicated perfluoropolyethers is the reaction of fluoroolefins with polyols, and the successive electrofluorination (see U.S. Pat. No. 3,962,348). Also in this case the process requires the use of HF which, as is well known, involves quite a number of technological and security problems.

There has now been found a very simple method which, in addition, does not show the previously mentioned disadvantages, and is suited for preparing the products of the invention.

An object of the present invention is to prepare compounds particularly suitable for electronic testing with a simpler process than is known in the art. See, for example, a class of compounds reported in published European patent application No. 203,348.

It is well known that the compounds suitable for this application have a large range between the pour point and the boiling temperature. In any case it is preferable that the pour point be as low as possible.

We have unexpectedly found that the perfluorinated compounds described in the formulae (I and II) have the properties indicated above. By using the process of the invention, applicants have found that it is possible to prepare compounds of formulae I and II with a good yield, and above all without other reaction products which are very difficult to separate for the product of the invention.

Thus, an object of the present invention is that of providing a process for obtaining halogenated polyethers of the formula:

$$R_FOCFX-CF_2-OR'_F \quad \text{and} \quad R_FO-CF-OR'_F$$
$$\quad\quad\quad\quad\quad\quad\quad\quad\quad\quad\quad\quad\quad\quad\quad |$$
$$\quad\quad\quad\quad\quad\quad\quad\quad\quad\quad\quad\quad\quad\quad\quad CF_2X$$

said process consisting in reacting a fluoroxy compound or a chloroxy compound of the formula: $R'_FOX$ with a fluorovinylether having formula: $R_FO-CF=CF_2$, wherein X, $R_F$ and $R'_F$ have the above indicated meanings, said reactants being used in stoichiometric quantities or, possibly, using an excess in perfluorovinylether.

The perfluorovinylether is in a liquid phase, possibly in the presence of an inert solvent, for instance chlorofluorohydrocarbons or perfluorohydrocarbons such as for example Algofrens 114 (dichlorotetrafluoroethane) and 115 (chloropentafluoroethane).

The temperature of the reaction may vary within a range of −30° C. and −140° C., but is preferably between −50° C. and −100° C.

The reaction is conducted keeping the temperature within the indicated range, in as much as it has been observed that this is quite indispensable for avoiding the easy occurrence of decomposition reactions of the hypofluorite or of other secondary reactions.

The fluoroxy (or chloroxy) compound is fed continuously in a gaseous phase, preferably diluted with an inert gas, such as for instance nitrogen, into a reactor containing the liquid perfluorovinylether.

The fluoroxy or the chloroxy compound may also be used in a liquid phase, preferably in the presence of an inert diluent, such as for example fluorochlorohydrocarbons.

Illustrating examples of fluoroxy and chloroxy compounds to be used as starting products in the process of the invention invention, are: fluoroxytrifluoromethane; chloroxytrifluoromethane; fluoroxypentafluoroethane; chloroxypentafluoroethane; fluoroxy-2-chloro-tetrafluoro; v-ethane; fluoroxy-2,2-dichlorotrifluoroethane; fluoroxy-2,2,2-trichloro-difluoroethane; fluoroxy-2-bromo-tetrafluoroethane; fluoroxy-heptafluoropropane; fluoroxy-perfluoro-n, propoxy-hexafluoropropane; fluoroxy-2-perfluoroethoxy-tetrafluoroethane; fluoroxy-2-perfluoromethoxy-tetrafluoroethane and their mixtures; fluoroxy-2-trifluoromethoxy-hexafluoropropane; and fluoroxy-2-tetrafluoroethoxy-hexafluoropropane.

Illustrating examples of perfluorovinylethers which can be used as starting products according to this invention include: perfluoromethyl-vinylether; perfluoroethylvinylether; perfluoropropylvinylether; perfluoro-n.butylvinylether; perfluoroisobutylvinylether; perfluorooctylvinylether; 4-iodineperfluorobutylvinylether; 3-iodineperfluoroethylvinylether; β-chloroperfluoroethylvinylether; γ-chloroperfluoropropylvinylether; perfluoro-3,6-dimethyl-1,4-dioxanyl-2-vinylether; perfluoro-2-n.propoxy-n.propylvinylether; perfluoro-2-methoxy-n.propylvinylether; perfluoro-2-ethoxy-n.propylvinylether.

The fluoroxy compounds are products well known from literature and more particularly they may be obtained according to a continuous process described in Italian Patent Application No. 19847 A/85.

The chloroxy compounds may be obtained according to any of the processes known to the Art, and more particularly may be obtained by the continuous process described in Italian Patent Application No. 21631 A/86.

The perfluoroalkylvinylethers are well known products and may be prepared by dehalogenation of the products described in Italian Patent Application No. 20781 A/85.

The perfluorinated polyethers of this invention are compounds well known for their exceptional thermal stability, their thermo-oxidative stability and stability to chemical agents, as well as for their unflammability property, and offer performances in highly diversified fields and under extremely severe operational conditions.

The perfluoropolyethers known to the Art, in general consist in mixtures of products from which it is difficult to obtain the single compounds. See GB 1,226,566. The perfluoropolyethers of the present invention, on the contrary, are obtainable as compounds, in general as isomeric mixtures having boiling points within a very narrow range of temperatures.

The perfluoropolyethers of the invention are particularly useful, as stated above, as fluids for testing in fields of electronics, for instance for leak-testing; thermal-shock testing, in hot-spot locations; and dew-point determination, etc.

The polyethers containing bromine and/or iodine polyethers are used as intermediates for the obtention of functionalized derivatives.

The following examples are given for purely illustrative purposes and shall in no way be construed as limiting the scope of the invention.

EXAMPLE 1

Into a reactor loaded with 75 ml of 1,2-dichlorotetrafluoroethane and 25 g of perfluoropropylvinylether, and cooled down to a temperature of $-75°$ C., were continuously fed in 2.5 Nl/h of $CF_3OF$ diluted with 1.5 Nl/h of $N_2$.

In the course of the reaction there were added further 148 g of perfluoropropylvinylether, while maintaining the reaction temperature constant at $-75°$ C.

After 5 hours and 30 minutes, the feeding in of the reactants was stopped and the condensate was subjected to distilling. Thereby were obtained 126 g of a 99% by weight fraction gathered in the temperature range of $61°-65°$ C. and having pour point of about $-138°$ C.

The yield was 60% in moles, calculated on the $CF_3OF$. The product was identified by means of mass-spectrometry, IR spectrophotometry, $^{19}F$ NMR and was found to consist of a mixture of:

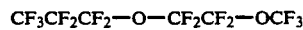

and

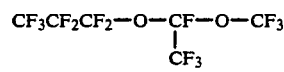

in a ratio of about from 26 to 74 between the linear and the branched isomer determined by gas-chromatography.

What we claim is:

1. A process for the preparation of halogenated polyethers of the formula:

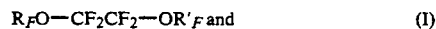 (I)

 (II)

wherein: $R_F$ and $R'_F$, either equal to or different from each other, are fluorinated alkyl radicals having from 1 to 20 carbon atoms; said process consisting in reacting a fluoroxy compound of the formula $R'_FOF$ with a flourovinylether of the formula $R_FO-CF=CF_2$, wherein $R_F$ and $R'_F$ are defined as above, at a temperature between $-30°$ C. and $-100°$ C., in the liquid phase in the presence of an inert solvent selected from chlorofluorohydrocarbons or perfluorohydrocarbons.

2. The process according to claim 1, wherein the fluoroxy compound is fed into the liquid reaction phase in a continuous way, in gaseous form, optionally diluted with an inert gas.

3. The process according to claim 1, wherein $R'_F$ is a perfluoromethyl radical.

4. The process according to claim 1, wherein $R_F$ is a perfluoropropyl radical.

* * * * *